United States Patent
Priessnitz et al.

(10) Patent No.: US 12,076,473 B2
(45) Date of Patent: Sep. 3, 2024

(54) DIALYSIS MACHINE AND ARRANGEMENT AND METHOD FOR HEATING A DIALYSIS SOLUTION

(71) Applicant: Fresenius Medical Care Deutschland GmbH, Bad Homburg (DE)

(72) Inventors: Bernd Priessnitz, Muerr (DE); Peter Wabel, Darmstadt (DE); Manuel Hassler, Frankfurt am Main (DE); Klaus Wolf, Muedesheim (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 354 days.

(21) Appl. No.: 16/636,049

(22) PCT Filed: Aug. 3, 2018

(86) PCT No.: PCT/EP2018/071205
§ 371 (c)(1),
(2) Date: Feb. 3, 2020

(87) PCT Pub. No.: WO2019/025623
PCT Pub. Date: Feb. 7, 2019

(65) Prior Publication Data
US 2020/0222612 A1    Jul. 16, 2020

(30) Foreign Application Priority Data
Aug. 4, 2017 (DE) .................. 10 2017 117 734.5

(51) Int. Cl.
*A61M 1/28* (2006.01)
*A61M 1/16* (2006.01)

(52) U.S. Cl.
CPC .......... *A61M 1/287* (2013.01); *A61M 1/1664* (2014.02); *A61M 2205/3368* (2013.01); *A61M 2205/3626* (2013.01)

(58) Field of Classification Search
CPC .... A61M 1/1664; A61M 1/287; A61M 1/166; A61M 1/1656; A61M 2205/3368;
(Continued)

(56) References Cited

U.S. PATENT DOCUMENTS

| | | | |
|---|---|---|---|
| 5,628,908 A | | 5/1997 | Kamen et al. |
| 5,993,053 A | * | 11/1999 | Clark ..................... B01F 25/50 366/144 |

(Continued)

FOREIGN PATENT DOCUMENTS

| | | | | |
|---|---|---|---|---|
| DE | 19752578 A1 | * | 6/1999 | .......... A61M 1/1664 |
| DE | 102008011828 | | 9/2009 | |

(Continued)

OTHER PUBLICATIONS

Machine generated translation of DE-19752578-A1 (Year: 1997).*

*Primary Examiner* — Magali P Slawski
*Assistant Examiner* — Bernadette Karen McGann
(74) *Attorney, Agent, or Firm* — Jacobson Holman PLLC

(57) ABSTRACT

A dialysis machine, in particular a peritoneal dialysis machine, has a heating device for heating a container containing a dialysis solution, in particular a peritoneal dialysis solution. The heating device is configured such that the heating of the dialysis solution by the heating device takes place non-uniformly at points.

9 Claims, 3 Drawing Sheets

(58) Field of Classification Search
CPC ...... A61M 2205/3626; A61M 2205/36; A61M 1/369; A61M 1/1662; A61M 5/44; A61M 5/445; B01F 33/12; G05D 23/1951; G05D 23/00; G05D 23/19; G05D 23/1928; F24H 9/1818; F24H 9/2021; F24H 9/2007; C02F 1/02; C02F 2201/007; C02F 2209/02; F28D 1/00
See application file for complete search history.

(56) References Cited

U.S. PATENT DOCUMENTS

| | | | |
|---|---|---|---|
| 2011/0000902 A1* | 1/2011 | Hedmann | A61M 1/167 219/494 |
| 2016/0082173 A1 | 3/2016 | Coll et al. | |
| 2018/0236157 A1* | 8/2018 | Wolf | A61M 1/282 |

FOREIGN PATENT DOCUMENTS

| | | | | |
|---|---|---|---|---|
| DE | 102015010467 | | 2/2017 | |
| DE | 102015010467 A1 * | | 2/2017 | ............ A61M 1/28 |
| EP | 2783747 | | 10/2014 | |
| WO | WO-2015173042 A1 * | | 11/2015 | ............ A47J 36/24 |
| WO | WO-2018187172 A1 * | | 10/2018 | .......... A61M 1/1656 |

\* cited by examiner a)

b)

DIALYSIS MACHINE AND ARRANGEMENT AND METHOD FOR HEATING A DIALYSIS SOLUTION

BACKGROUND OF THE INVENTION

1. Field of the Invention

The present invention relates to a dialysis machine, in particular to a peritoneal dialysis machine, and to an arrangement and to a method for heating a dialysis solution, in particular a peritoneal dialysis solution.

2. Description of Related Art

It is known from the prior art to heat the peritoneal dialysis solution, also called a "dialysis solution" in the following, to be supplied to the patient in the course of a peritoneal dialysis treatment. The desired temperature in this respect is typically at body temperature, i.e. at approximately 37°. In order not to impair the well-being of the patient and to avoid injuries due to too high a temperature of the dialysis solution, there is a need to heat the solution to be administered to the patient as homogeneously as possible, i.e. free of temperature gradients.

It is thus the underlying object of the present invention to provide a possibility by which a heating of the dialysis solution to be supplied to the patient is achieved that is as homogeneous as possible.

SUMMARY OF THE INVENTION

This object is achieved by a dialysis machine, in particular by a peritoneal dialysis machine, having the features of claim 1, by an arrangement in accordance with claim 8, and by a method in accordance with claim 10.

Provision is accordingly made that the dialysis machine has a heating device for heating a container containing a dialysis solution, wherein the heating device is configured such that the heating of the dialysis solution takes place non-uniformly at points. It is achieved by the non-uniform heating, i.e. the spatially non-homogeneous heating, of the dialysis solution that a temporary temperature gradient is formed in the dialysis solution. This causes flow movements such as barrel-like flows that are caused by free convection. These flow movements in turn have the result that an intermixing of the dialysis solution takes place without mechanical means such as vibrators or a manual intermixing of the container having to be used. Hot spots within the dialysis solution can thus be prevented.

The dialysis machine is preferably a peritoneal dialysis machine. However, any other desired dialysis machines are also covered by the invention. The dialysis solution is equally, however, preferably, but not necessarily, a peritoneal dialysis solution.

The intermixing naturally not only has the effect of a homogenization of the temperature, but also that of a homogenization of the concentration of the substances dissolved in the dialysis solution.

The container is preferably a bag. However, any other desired containers are also covered by the invention.

In a preferred embodiment of the invention, the dialysis machine has a receiver for the container such as a tray, a plate or the like, with the heating device being arranged at the receiver and being non-uniformly, i.e. non-homogeneously, distributed over the receiver. It is thus conceivable, for example, that only that region of the container and thus of the dialysis solution is heated that is located in the region of the heating device, but no other regions. As stated above, a temporary temperature gradient is thereby generated that in turn causes a flow movement and thus an intermixing of the dialysis solution.

It is possible in this manner to only heat one section of the receiver and thus of the dialysis solution, for example, but not a different section of the receiver.

Provision can alternatively or additionally be made that a heating device is provided that is arranged at different regions of the receiver and that has regions that are operated with different power, whereby the regions of the heating device transfer different heat quantities to the dialysis solution.

It can also thereby be achieved that the dialysis solution is non-uniformly heated. This has the result that a temporary temperature gradient is adopted within the dialysis solution that in turn results in an intermixing of the dialysis solution by free convection. A uniform temperature can thus be obtained within the dialysis solution before it is administered to the patient.

It is, for example, conceivable that the energy input by the heating device does not take place constantly over the heating surface, but rather non-linearly so that a convection flow such as a barrel-like flow is even amplified.

A temporary temperature gradient within the solution can also be achieved in that a heating device is provided that has regions that are operated with a time lag. It is thus conceivable, for example, that initially only one or more regions are operated, which has the consequence that only a portion of the dialysis solution is heated, but not another portion. The temperature gradient resulting from this generates a convection flow. One or more further regions of the heating device are switched in at a certain point in time after a switching on of a first region of the heating device to achieve a heating of the dialysis solution that is as uniform as possible.

It is particularly preferred if a receiver for the container is provided that is inclined with respect to the horizontal. The effect can be utilized in this respect that the cooler dialysis solution flows downwardly, i.e. toward the region of the container directed downwardly, while warm dialysis solution flows upwardly, i.e. toward the region of the container directed upwardly. In this manner, a barrel-like flow can be achieved within the dialysis solution that results in an intermixing and thus a homogenization of the temperature of the dialysis solution.

One or more temperature sensors are preferably provided that detect the temperature of the heating device and/or of the receiver for the container and/or of the container itself. A control or regulation unit can furthermore be provided that controls or regulates the power of the heating device or different regions therefrom in dependence on the value or values measured.

The present invention further relates to an arrangement for heating a dialysis solution comprising a receiver at which a heating device is arranged and on which a container is located that contains the dialysis solution, with the container being arranged in the receiver such that it regionally projects over the heating device of the receiver. Temperature gradients arise in that the overhanging region remains comparatively cold and the heated region has a correspondingly higher temperature.

The arrangement in accordance with the invention is preferably configured in accordance with the features of one of the claims 1 to 7.

The arrangement can thus have a receiver for the container, with the heating device being arranged at the receiver and being non-uniformly distributed over the receiver.

Provision can furthermore be made that the heating device has different regions and that a control unit is provided that is configured to operate the different regions of the heating device at different powers and/or with a time offset.

It is furthermore conceivable that the arrangement does not have any mechanical device for intermixing the dialysis solution contained in the container.

The receiver of the arrangement for the container is preferably inclined with respect to the horizontal.

The present invention furthermore relates to a method of heating a dialysis solution, wherein the container containing the dialysis solution is heated by a heating device such that the heating of the dialysis solution takes place non-uniformly at points.

Provision is preferably made in this respect that the container is arranged in a receiver comprising the heating device such that the container projects over the heating device at regions. It is, for example, conceivable for the bag, etc. to project over the heating device by ⅓.

An accelerated convection flow is produced by an asymmetrical arrangement of the container relative to the hot plate and a uniform intermixing of the solution in the bag, etc. is thus already carried out during the heating. This is in particular of advantage with heating systems in which no temperature sensor is provided at the inflow port to the patient, which represents a preferred embodiment of the invention. It can be ensured by the forced flow formation that the solution flowing to the patient is not subject to any larger temperature fluctuations, whereby an active intermixing of the bag, etc. after the heating can be omitted.

The containers/bags can also be arranged above one another/in stacked form, whereby a flow is formed in the two or more containers and thus a homogenous intermixing is also achieved.

If two bags are above one another, there is also the possibility of a cooling, i.e. a barrel-like flow can also be generated by the position of the upper bag. The bags can also be placed above one another in an offset manner in this respect.

The container can be arranged in a receiver that has a heating device, wherein the heating device has regions that are non-uniformly distributed in the receiver so that the container located in the receiver is heated non-uniformly.

It is furthermore conceivable that the container is arranged in a receiver that has a heating device that has regions that are operated at different powers and/or at different times so that they produce a different heating power or a heating power changing over time.

An arrangement of simple design results when the dialysis solution located in the container is not mechanically intermixed, but rather solely on the basis of the convection flow.

Provision can finally be made that a heating device is provided and that the temperature of the heating device and/or the temperature of the receiver for the container and/or the temperature of the container is detected, and that the different regions are controlled or regulated in dependence on the value or values measured.

It is generally also conceivable and covered by the invention to measure the temperature of the dialysis solution itself and to control or regulate the heating device based thereon.

The heating device can be configured in one part or in multiple parts.

It is conceivable for the receiver to have a thermally conductive base on which the container is located.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
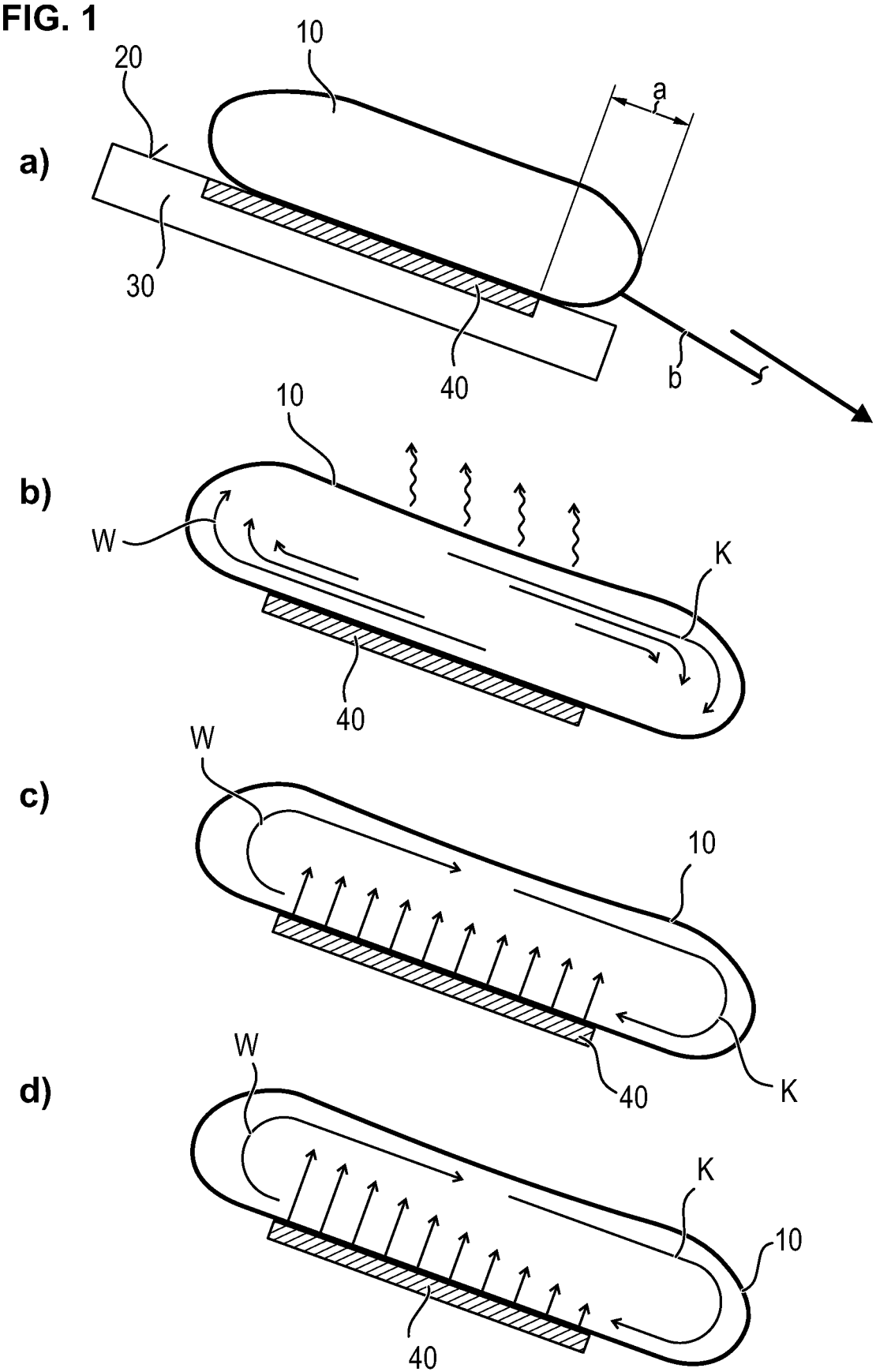
FIG. 1: schematic representations of arrangements with a receiver, a heating device and a bag.

FIG. 1 *a*) shows a bag containing a dialysis solution by reference numeral 10. The bag is located on a support surface 20 of the receiver 30 designed as a slanted surface. Reference numeral 40 shows the heating device in the form of a hot plate that is embedded into the receiver 30 and terminates at its upper side. A line section is marked by reference symbol b that leads to the patient in accordance with the direction of the arrow. Reference symbol a marks the bag section that projects beyond the hot plate 40.

Volumes of 1-10 l, preferably of 2 to 8 l, can be used for the containers. Other volumes are, however, likewise conceivable.

Elements that are the same or have the same function are marked by the same reference numerals in the Figures.

An embodiment can be seen from FIG. 1 *b*) in which the bag 10 is larger than the receiver or than the heating device 40. The bag 10 thus projects beyond the receiver 30 both at its upper end and at its lower end. Reference symbol W marks the warm solution and reference symbol K marks the solution that is cold with respect to it. The first rises and the latter falls so that a circle or a barrel-like flow marked by arrows results within the bag 10 that ultimately produces a good intermixing and thus a homogeneous temperature distribution within the bag.

FIG. 1 *c*) shows an embodiment in which the hot plate 40 produces a constant power over its length so that a constant thermal input takes place as is symbolized by the arrows of equal length. In contrast, FIG. 1 *d*) shows an embodiment in which a spatially non-uniform energy input takes place, with the thermal input in the region inclined upwardly being larger than in the region inclined downwardly.

Figure 2:
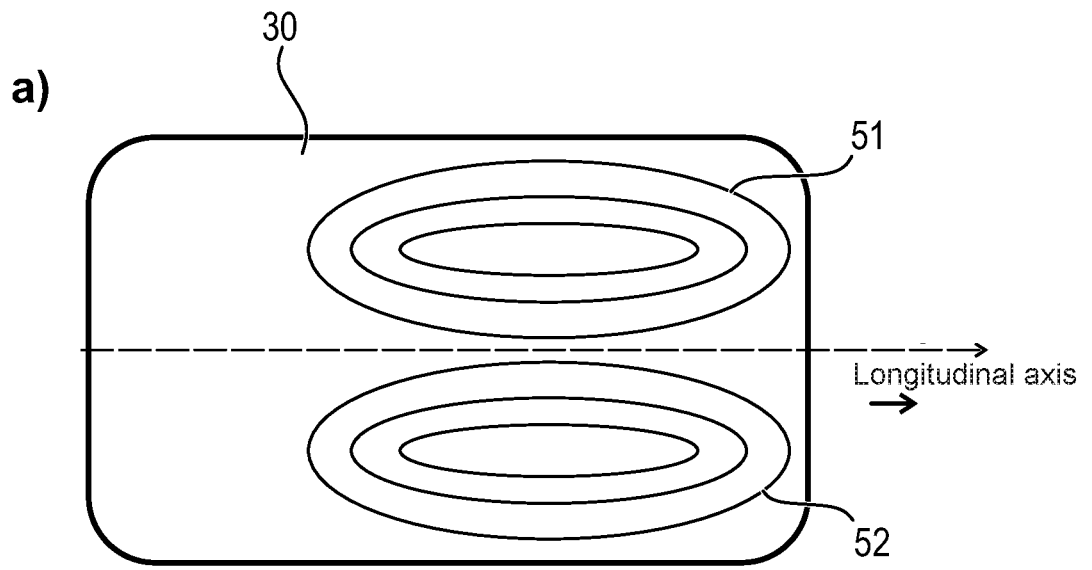
FIG. 2: plan views of receivers with differently arranged heating devices.
Figure 2:
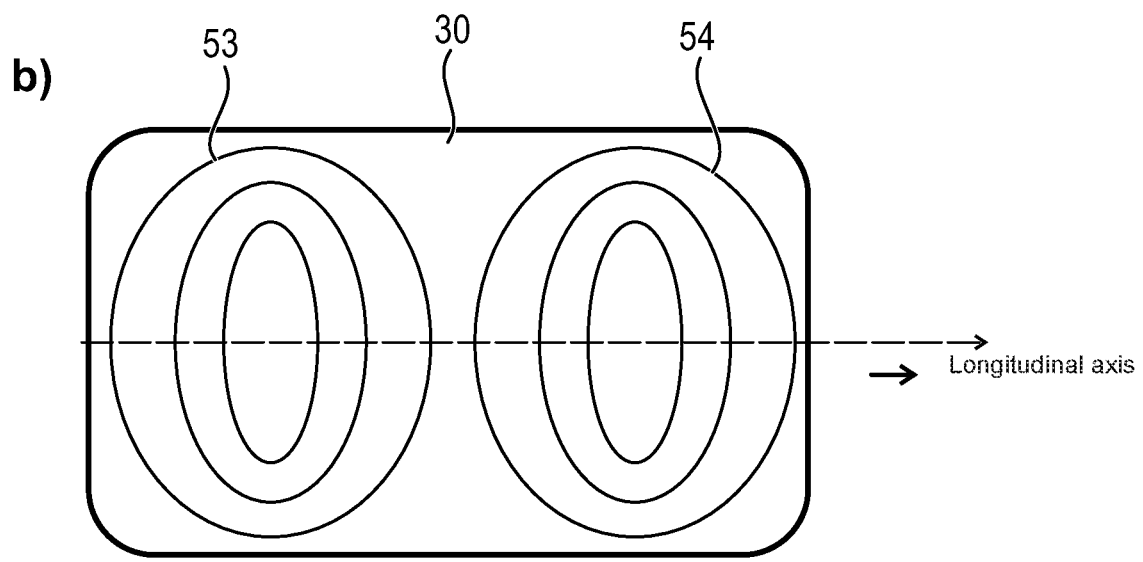

Two plan views of receivers 30 whose heating devices respectively have two heating elements 51, 52 in accordance with FIG. 2 a) can be seen from FIG. 2. In accordance with FIG. 2 a), these heating coils extend lengthways, i.e. along the longitudinal axis of the receiver 30 that faces in the direction of the inclination of the heating surface. The heating elements are, however, not located in the total receiver 30; the region of the receiver shown at the left is designed without a heating device. A temperature gradient that drives a convection flow of the solution is generated in the dialysis solution by the asymmetrical embodiment of the heating elements 51, 52 under a thermally conductive surface. This produces a homogeneous intermixing of the dialysis solution.

The active heating surface can also be designed as a singular heating element. In this respect, the one heating element can then only be located in the lower part or also only in the upper part.

The inclination of the heating surface along the longitudinal axis is also indicated by the arrow in FIG. 2 b). In accordance with FIG. 2 b), the heating coils 53, 54 are oriented transversely to the longitudinal axis and have separately controllable segments.

A heating element, e.g. the element 53, is activated at a time t=0 to generate a temperature gradient. The latter generates a convection flow in the dialysis solution.

The second heating coil 54 is switched in at a later time t=1 to enable a heating of the solution that is as effective as possible. The gradient can be checked by temperature sensors in both segments 53, 54 and the gradient and/or the convection can be monitored by a targeted switching off and on of the elements. The intermixing can also be implemented in a horizontally arranged heating plate or receiver by this embodiment.

Figure 3:
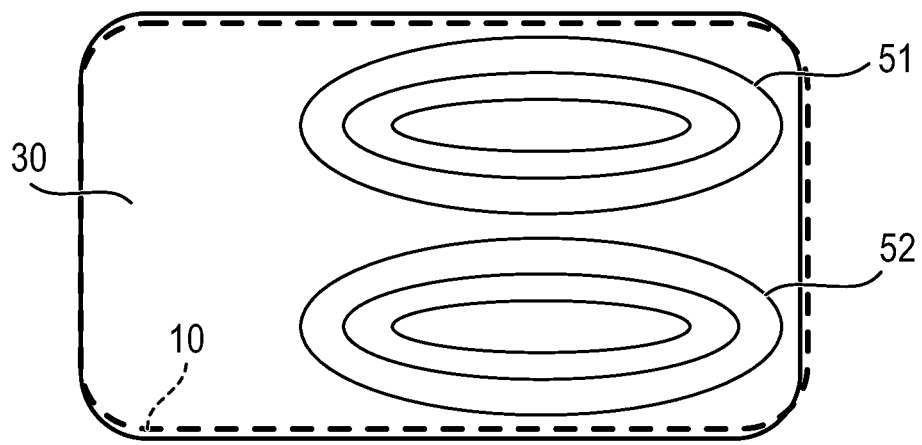
FIG. 3: a further plan view of a receiver with a heating device.

FIG. 3 shows an embodiment in accordance with FIG. 2 a), with the active heating surface, approximately 70% of the visible hot plate or support surface of the receiver comprising a thermally conductive material. The bag 10 is shown as dashed.

In an embodiment, the total power of the heating device amounts to 400 W. Temperature sensors that check the heating process are located at the center of the heating plate. The sensors have a target temperature of 39° C. A 6 l solution bag that has been completely placed on is heated over a time period of 180 minutes. The bag reaches a surface temperature of 38° C. after approximately 112 minutes.

Figure 4:
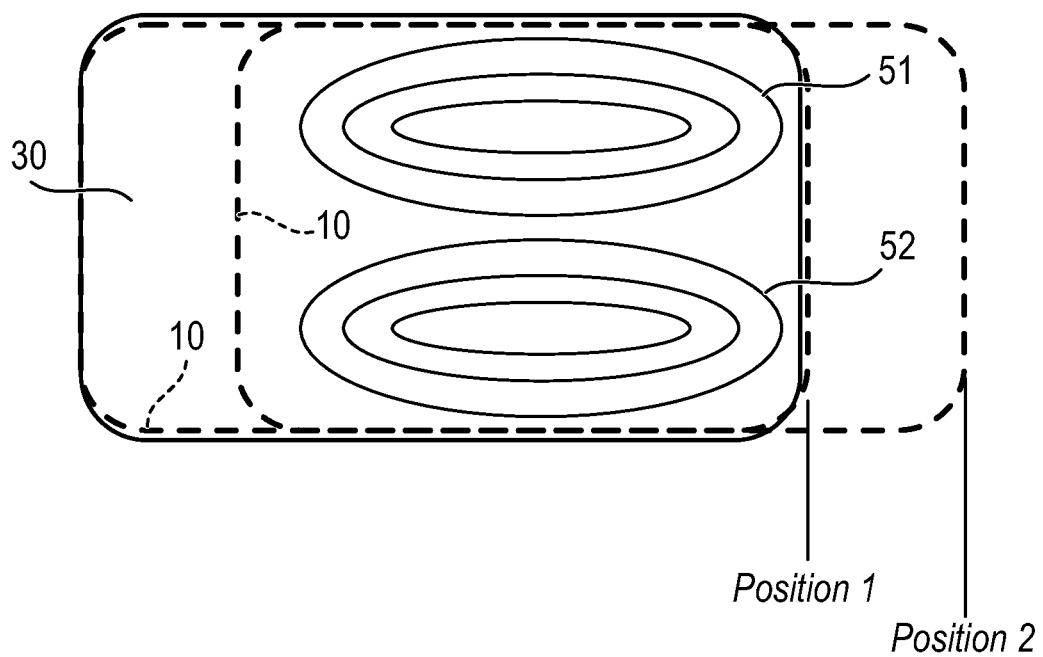
FIG. 4: a plan view of a receiver with a heating device with a bag arranged at different positions.

A bag 10 located on the receiver can be seen in two different positions from FIG. 4.

Position 1 corresponds to that in accordance with FIG. 3.

In position 2, the right marginal region of the bag 10 projects beyond the heating device. A temperature gradient and thus a convection flow are also thereby achieved, whereby a homogeneous heating and intermixing of the dialysis solution is achieved.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A dialysis machine comprising:
an assembly including a positionable container containing a dialysis solution that is to be heated and a heating device for heating the container, the heating device including a plurality of regions and a control unit, and the container being positioned in an asymmetrical arrangement relative to the heating device; and
a receiver for receiving the container, with at least one of the heating device and the receiver being inclined with respect to the horizontal,
the control unit being configured to operate the plurality of regions of the heating device at different levels of power so as to transfer different quantities of heat,
such that the heating of the dialysis solution by the heating device takes place non-uniformly at points throughout the dialysis solution so as to provide a temporary temperature gradient in the dialysis solution.

2. The dialysis machine in accordance with claim 1, wherein the heating device is arranged at the receiver and is distributed non-uniformly over the receiver.

3. The dialysis machine in accordance with claim 1, wherein the heating device that provides the temporary temperature gradient effects convective flow of the dialysis solution within the container, which provides for intermixing of the non-uniformly heated points throughout the dialysis solution.

4. The dialysis machine in accordance with claim 1, wherein the control unit is configured to operate the plurality of regions of the heating device with a time offset.

5. The dialysis machine in accordance with claim 1, further comprising one or more temperature sensors that detect the temperature of the heating device and/or the temperature of the receiver for the container and/or the temperature of the container itself, the control unit being configurable to operate the heating device in dependence on the value or values measured.

6. The dialysis machine according to claim 1, wherein the dialysis machine is a peritoneal dialysis machine.

7. The dialysis machine according to claim 1, wherein the dialysis solution is a peritoneal dialysis solution.

8. The dialysis machine according to claim 1, wherein the container is arranged in the receiver such that a portion of the container other than an overhanging portion of the container projects over the heating device.

9. The dialysis machine according to claim 1, wherein the heating device that provides the temporary temperature gradient effects convective flow of the dialysis solution within the container, which provides for homogenization of a concentration of substances dissolved in the dialysis solution.

* * * * *